(12) United States Patent
Hibst et al.

(10) Patent No.: US 6,989,454 B2
(45) Date of Patent: Jan. 24, 2006

(54) METHOD FOR PRODUCING MALEIC ANHYDRIDE

(75) Inventors: Hartmut Hibst, Schriesheim (DE); Ralf Noe, Mannheim (DE); Kai Michael Exner, Eppelheim (DE); Mark Duda, Ludwigshafen (DE)

(73) Assignee: BASF - Aktiengesellschaft, Ludwigshafen (DE)

( * ) Notice: Subject to any disclaimer, the term of this patent is extended or adjusted under 35 U.S.C. 154(b) by 3 days.

(21) Appl. No.: 10/485,200

(22) PCT Filed: Jul. 17, 2002

(86) PCT No.: PCT/EP02/07935

§ 371 (c)(1),
(2), (4) Date: Jan. 29, 2004

(87) PCT Pub. No.: WO03/014100

PCT Pub. Date: Feb. 20, 2003

(65) Prior Publication Data

US 2004/0236120 A1    Nov. 25, 2004

(30) Foreign Application Priority Data

Aug. 1, 2001    (DE) ................. 101 37 534

(51) Int. Cl.
*C07D 307/36*    (2006.01)
(52) U.S. Cl. .................................. 549/262
(58) Field of Classification Search ........... 549/262
See application file for complete search history.

(56) References Cited

U.S. PATENT DOCUMENTS

| | | |
|---|---|---|
| 3,147,084 A | 9/1964 | Franzen et al. |
| 3,893,951 A | 7/1975 | Grasselli et al. |
| 3,904,653 A | 9/1975 | Milberger et al. |
| 3,907,834 A | 9/1975 | Milberger et al. |
| 3,911,039 A | 10/1975 | Grasselli et al. |
| 3,919,257 A | 11/1975 | Milberger et al. |
| 3,932,551 A | 1/1976 | Grasselli et al. |
| 4,021,427 A | 5/1977 | Dolhyj et al. |
| 4,075,232 A | 2/1978 | Zagata et al. |
| 4,115,441 A | 9/1978 | Shaw et al. |
| 4,138,366 A | 2/1979 | Shaw et al. |
| 4,155,920 A | 5/1979 | Milberger et al. |
| 4,157,987 A | 6/1979 | Dolhyj et al. |
| 4,162,234 A | 7/1979 | Grasselli et al. |
| 4,170,570 A | 10/1979 | Zagata et al. |
| 4,203,906 A | 5/1980 | Takada et al. |
| 4,250,054 A | 2/1981 | Shaw et al. |
| 4,359,407 A | 11/1982 | Dolhyj et al. |
| 4,378,309 A | 3/1983 | Shaw et al. |
| 4,423,281 A | 12/1983 | Yamamoto et al. |
| 4,424,141 A | 1/1984 | Grasselli et al. |
| 4,547,615 A | 10/1985 | Yamamoto |
| 5,168,090 A | 12/1992 | Ebner et al. |

FOREIGN PATENT DOCUMENTS

| | | |
|---|---|---|
| DE | 2 241918 | 3/1973 |
| DE | 2 322 186 | 11/1973 |
| DE | 24 47 825 | 7/1975 |
| DE | 24 59 092 | 7/1975 |
| DE | 25 30959 | 2/1976 |
| DE | 26 03770 | 9/1976 |
| DE | 25 39106 | 3/1977 |
| DE | 27 02 606 | 7/1978 |
| DE | 28 13 424 | 10/1978 |
| DE | 28 30765 | 1/1980 |
| EP | 911 313 | 4/1999 |
| EP | 1 097 745 | 5/2001 |
| WO | 97/43234 | 11/1997 |
| WO | 97/43242 | 11/1997 |

OTHER PUBLICATIONS

Ullmann's Enc.Ind.Chem.6thEd, 1999, Electronic Release, Chapter Maleic and Fumaric Acid.
E. Bordes, Cat. Today 16, 1993, 27-38.
Yoshioka, Hydrocarbon Processing 63, Nov. 1984, 97-100.
Derwent JP 05057188.

*Primary Examiner*—Paul A. Zucker
(74) *Attorney, Agent, or Firm*—Novak Druce & Quigg, LLP

(57) ABSTRACT

A process for preparing maleic anhydride by heterogeneously catalyzed gas-phase oxidation of an n-butene-containing hydrocarbon stream by means of oxygen-containing gases in a shell-and-tube reactor having two successive reaction zones, where the first, feed-side reaction zone contains at least one catalyst which is suitable for the oxydehydrogenation of n-butenes to 1,3-butadiene and the second, product-side reaction zone contains at least one catalyst which is suitable for the oxidation of 1,3-butadiene to maleic anhydride, is carried out using a shell-and-tube reactor which has at least one heat transfer medium circuit in the region of the first, feed-side reaction zone and at least one further heat transfer medium circuit in the region of the second, product-side reaction zone.

9 Claims, No Drawings

METHOD FOR PRODUCING MALEIC ANHYDRIDE

Preparation of Maleic Anhydride

The present invention relates to a process for preparing maleic anhydride by heterogeneously catalyzed gas-phase oxidation of an n-butene-containing hydrocarbon stream by means of oxygen-containing gases in a shell-and-tube reactor having two successive reaction zones, where the first, feed-side reaction zone contains at least one catalyst which is suitable for the oxydehydrogenation of n-butenes to 1,3-butadiene and the second, product-side reaction zone contains at least one catalyst which is suitable for the oxidation of 1,3-butadiene to maleic anhydride.

Maleic anhydride is an important intermediate in the synthesis of γ-butyrolactone, tetrahydrofuran and 1,4-butanediol, which are in turn used as solvents or are processed further, for example to produce polymers such as polytetrahydrofuran or polyvinylpyrrolidone.

The preparation of maleic anhydride by single-stage heterogeneously catalyzed gas-phase oxidation of n-butenes or n-butane by means of oxygen in the presence of a vanadium-, phosphorus- and oxygen-containing catalyst is generally known and is described, for example, in Ullmann's Encyclopedia of Industrial Chemistry, $6^{th}$ edition, 1999 Electronic Release, Chapter "MALEIC AND FUMARIC ACID—Maleic Anhydride". In the case of the gas-phase oxidation of n-butane using air, a maleic anhydride selectivity of about 60% is achieved at an n-butane conversion of 85% (cf. E. Bordes, Catal. Today 16, 1993, pages 27 to 38).

A disadvantage of the use of n-butane is its often unsatisfactory availability at the location of the plant and the logistic problems resulting therefrom. For this reason, n-butenes which are, for example, present in ample quantities in the $C_4$ fraction from a steamcracker are also of interest as starting materials for the economical production of maleic anhydride. In the abovementioned gas-phase oxidation of n-butenes over the stated vanadium-, phosphorus- and oxygen-containing catalysts, the yield of maleic anhydride is restricted to values of about 50 mol %. E. Bordes reports an achievable maleic anhydride selectivity of 50 mol % at a 1-butene conversion of 95% (cf. E. Bordes, Catal. Today 16, 1993, pages 27 to 38). In addition, the selective oxidation of n-butenes to maleic anhydride forms a series of undesirable by-products compared to the selective oxidation of n-butane.

A further starting material known for the preparation of maleic anhydride is 1,3-butadiene. Thus, DE-A 2 241 918 describes the gas-phase oxidation of 1,3-butadiene to maleic anhydride in the presence of molybdenum-, antimony- and oxygen-containing catalysts. Disadvantages of the direct use of pure 1,3-butadiene are its unsatisfactory availability and its high price.

An inexpensive possibility for preparing a 1,3-butadiene-containing stream is the oxydehydrogenation of n-butenes or n-butene-containing streams. Thus, A. Yoshioka et al. in Hydrocarbon Processing, 63, November 1984, pages 97 to 100, describe the oxydehydrogenation of a raffinate II stream to give a 1,3-butadiene yield of 78%.

DE-A 26 03 770 describes the preparation of maleic anhydride by reaction of n-butenes with air in a fluidized-bed reactor in the presence of an oxidation catalyst which is effective in the oxydehydrogenation of n-butenes to 1,3-butadiene and an oxidation catalyst which is effective in the oxidation of 1,3-butadiene to maleic anhydride. A disadvantage of this process is a low maleic anhydride yield of 30%.

DE-A 25 39 106 teaches the preparation of maleic anhydride by reaction of n-butane and n-butene-containing streams with air in a shell-and-tube reactor having an undivided, isothermal reaction zone containing two different catalysts. The catalyst present on the feed side oxydehydrogenates n-butane and n-butene to 1,3-butadiene. The catalyst present on the product side oxidizes the 1,3-butadiene formed to maleic anhydride. A maleic anhydride yield of 60% was achieved using a cis- and trans-2-butene mixture and an oxydehydrogenation catalyst based on bismuth molybdate and an oxidation catalyst based on antimony molybdate.

According to the present invention, it has been recognized that the above-described direct connection of oxydehydrogenation and oxidation in series and, in particular, isothermal operation of both processes results in many disadvantages. Furthermore, it has been recognized, according to the present invention, that very different reaction temperatures are required for optimal operation of the oxydehydrogenation of n-butenes to 1,3-butadiene and of the oxidation of 1,3-butadiene to maleic anhydride. In addition, the amounts of heat evolved in the two reaction steps are very different. While only about 130 kJ/mol are liberated in the oxydehydrogenation of n-butenes to 1,3-butadiene, the oxidation of 1,3-butadiene to maleic anhydride releases about 990 kJ/mol. Heat removal matched to the evolution of heat is thus not possible in reality. Furthermore, matching to the optimum operating conditions of the two catalysts is likewise not possible or possible only to a very limited extent. Thus, effects due to different catalyst activities, to deactivation processes proceeding at different rates, to fluctuations in the purity and quality of the feed stream or to load changes (changes in the flow velocity and/or the feed rate) can be corrected only to a very restrictive extent, if at all.

It is an object of the present invention to develop a process for preparing maleic anhydride by heterogeneously catalyzed gas-phase oxidation of an inexpensive and readily available hydrocarbon stream by means of oxygen, which process does not have the abovementioned disadvantages and makes possible a high conversion, a high selectivity and a high yield of desired product at a high hydrocarbon throughput over the catalyst and thus gives a high space-time yield. A further object of the present invention is to allow flexible operation which makes it possible to achieve a high space-time yield over a long period of time even in the case of fluctuations in the amount, quality or purity of the starting materials or in the event of progressive catalyst deactivation.

We have found that this object is achieved by a process for preparing maleic anhydride by heterogeneously catalyzed gas-phase oxidation of an n-butene-containing hydrocarbon stream by means of oxygen-containing gases in a shell-and-tube reactor having two successive reaction zones, where the first, feed-side reaction zone contains at least one catalyst which is suitable for the oxydehydrogenation of n-butenes to 1,3-butadiene and the second, product-side reaction zone contains at least one catalyst which is suitable for the oxidation of 1,3-butadiene to maleic anhydride, wherein the shell-and-tube reactor has at least one heat transfer medium circuit in the region of the first, feed-side reaction zone and at least one further heat transfer medium circuit in the region of the second, product-side reaction zone.

For the purposes of the present invention, the term "shell-and-tube reactor" refers to a reactor which contains at least one reaction tube which is surrounded by a heat transfer medium for the purpose of heating and/or cooling. In general, shell-and-tube reactors used industrially contain from a few hundred to tens of thousands of reactor tubes connected in parallel. If a number of individual shell-andtube reactors (in the sense of shell-and-tube reaction apparatuses) are connected in parallel, these should be regarded as the equivalent of one shell-and-tube reactor and are hereinafter encompassed by the term shell-and-tube reactor.

For the purposes of the present invention, the term first, feed-side reaction zone is the region within the shell-and-tube reactor which contains at least one catalyst suitable for the oxydehydrogenation of n-butenes to 1,3-butadiene. The term second, product-side reaction zone is the region within the shell-and-tube reactor which contains at least one catalyst suitable for the oxidation of 1,3-butadiene to maleic anhydride.

In the process of the present invention, it is essential to use a shell-and-tube reactor which has one heat transfer medium circuit in the region of the first, feed-side reaction zone and a further heat transfer medium circuit in the region of the second, product-side reaction zone. Thus, for example, each of the two reaction zones can be heated/cooled by means of one, two or three or more heat transfer medium circuits. Preference is given to using a shell-and-tube reactor which has precisely one heat transfer medium circuit in the region of the first reaction zone and precisely one heat transfer medium circuit in the region of the second reaction zone.

Shell-and-tube reactors used in the process of the present invention can in principle be any known shell-and-tube reactors having two or more heat transfer medium circuits. Preference is given to using shell-and-tube reactors having two heat transfer medium circuits. Suitable shell-and-tube reactors are described, for example, in U.S. Pat. No. 3,147,084, DE-C 28 30 765, EP-A 0 911 313 and EP-A 1 097 745.

In general, the shell-and-tube reactors which can be used in the process of the present invention comprise an outer reactor body having connections for the introduction and discharge of the reaction gases at the top and bottom. The upper and lower ends of the reactor tubes are welded into upper and lower tube plates. The space surrounding the reactor tubes between the upper and lower tube plates is generally divided into two zones by means of a dividing plate. Each of the two zones usually has two connections on the reactor body for the introduction and discharge of the heat transfer medium. In general, the dividing plate is located at the height of the transition region between the two successive reaction zones.

In one embodiment, the dividing plate can, as described in U.S. Pat. No. 3,147,084, be fixed to the reactor tubes and seal the two heat transfer medium zones from one another.

In another embodiment, the dividing plate can have a very small gap between it and the individual reactor tubes so as to allow unhindered thermal expansion of the reactor tubes and thus prevent mechanical stresses and consequent corrosion and mechanical damage. Such a construction is described, for example, in DE-C 28 30 765. In a further embodiment, the reactor tubes are widened in the direction of the dividing plate in the region of the dividing plate in order to achieve a further reduction in the gap between the tube and the reaction plate. The hole through the dividing plate can be provided on its inside with additional corrugations to improve the seal between the two heat exchange media, as described in EP-A 1 097745. It is also possible for the dividing plate to be fixed to the reactor tubes but to have an annular gap between it and the reactor body. To avoid mechanical stresses due to nonuniform thermal expansion, the reactor body can also be equipped with expansion zones, for example in the form of semicircular recesses. A reactor constructed in such a way is described, for example, in EP-A 1 097 745.

The reactor tubes in the abovementioned shell-and-tube reactors are usually made of ferritic steel and typically have a wall thickness of from 1 to 3 mm. Their internal diameter is generally from 15 to 30 mm. The number of reactor tubes per shell-and-tube reactor is usually in the range from 5000 to 35 000, although a number above 35 000 can also be employed in particularly large plants. The reactor tubes are normally distributed uniformly within the reactor body.

The heat transfer medium zones may also contain various internals for directing the flow of the heat transfer medium. Preference is given to internals which deflect at least part of the circulating heat transfer medium in a radial direction, i.e. within the cross section, and thus allow largely perpendicular, i.e. radial, flow onto the reactor tubes running in the axial direction. Preference is given to internals which promote essentially meandering flow of at least part of the heat transfer medium. Explicit mention may be made of an alternative arrangement of "donut-shaped" deflecting plates having a central hole through which fluid can flow and circular deflection plates having a gap for the flow of fluid between the reactor body and the deflection plate, as described, for example, in EP-A 1 097 745.

Suitable heat exchange media are, in particular, fluid cooling/heating media. The use of salt melts, e.g. potassium nitrate, potassium nitrite, sodium nitrate and/or sodium nitrite, or of low-melting metals such as sodium or alloys of various metals is particularly useful. Preference is given to using salt melts.

The direction of flow of the heat transfer medium in the reactor can in principle be either from the top downward or from the bottom upward and can be chosen independently for the two reaction zones. For hydrodynamic reasons, especially because of the induced convection, flow of the heat transfer medium from the bottom upward in the reactor is preferred in the process of the present invention.

The reaction gas can flow through the shell-and-tube reactors which can be used in the process of the present invention either from the top downward or from the bottom upward. In the first-named case, the catalyst which is suitable for the oxydehydrogenation of n-butenes to 1,3-butadiene is present in the upper reaction zone and the catalyst which is suitable for the oxidation of 1,3-butadiene to maleic anhydride is located in the lower reaction zone. In the second case, the catalyst is arranged in the converse manner.

If the heat transfer medium flows in the same direction as the reaction gas, this is referred to as cocurrent operation; if the heat transfer medium flows in the opposite direction, this is referred to as countercurrent operation. In the process of the present invention, preference is given to cocurrent operation, since this generally allows better distribution of the hot spot.

On the basis of the preferred flow of heat transfer medium from the bottom upward and a countercurrent mode of operation, upward flow of the reaction gases and the two heat exchange media is particularly preferred in the process of the present invention.

Furthermore, the shell-and-tube reactor to be used can also contain one or more integrated or upstream preheating zones which heat the gas mixture entering the reactor. A preheating zone integrated into a shell-and-tube reactor can be achieved, for example, by means of reactor tubes which are filled with inert material and may be surrounded by a heat transfer medium. As inert material, it is in principle possible to use all materials which do not contribute to the chemical reaction of the reaction gas flowing through them, i.e. do not induce or catalyze a heterogeneously catalyzed reaction, and which result in a maximum pressure drop below the maximum value tolerable in the case of the specific plant. Suitable materials are, for example, oxidic materials-, e.g. $Al_2O_3$, SiC, or metallic materials, e.g. stainless steel. The inert material can be present, for example, in the form of shaped bodies, meshes, open sponges and knitteds or internals as are customarily also used in static mixers. Preference is given to shaped bodies such as spheres, pellets, hollow cylinders, rings, trilobes, tristars, wagon wheels, extrudates or irregular, crushed bodies.

In the process of the present invention, the catalysts of the two successive reaction zones can, for example, follow one another directly or be separated from one another by an empty space or an intermediate bed. The transition between the two catalysts, the empty space or the intermediate bed is in each case preferably at the approximate height of or in the vicinity of the dividing plate.

In the process of the present invention, the reaction gas from the first, feed-side reaction zone is preferably passed through an inert intermediate bed before it enters the second, product-side reaction zone. Inert materials suitable for this intermediate bed are generally materials which do not, under the prevailing reaction conditions, contribute significantly to chemical reaction of the reaction gas flowing through the bed, i.e. do not induce or catalyze a heterogeneously catalyzed reaction, and which result in a maximum pressure drop below the maximum which can be tolerated in the specific plant. Examples of suitable materials are oxidic materials, e.g. $Al_2O_3$, SiC, or metallic materials, e.g. stainless steel. The inert material can be present, for example, in the form of shaped bodies, meshes, open sponges and knitteds or internals as are customarily also used in static mixers. Preference is given to shaped bodies such as spheres, pellets, hollow cylinders, rings, trilobes, tristars, wagon wheels, extrudates or irregular, crushed bodies. The maximum diameter of the preferred shaped bodies is preferably from 1/10 to at most 1/1 of the internal diameter of the reactor tubes.

Depending on whether the second reaction zone is operated at a higher or lower temperature, the inert intermediate layer makes heating or cooling of the reaction gas possible. To enable this to be achieved, the major part of the inert intermediate bed is generally in the region of the second, hotter or colder zone. Furthermore, the inert intermediate bed allows precipitation of relatively high molecular weight by-products from the first reaction zone and counters deposition on the catalyst of the second reaction zone and thus a gradual increase in the pressure drop due to such deposits on the catalyst.

The length of the intermediate bed is preferably such that the major part of the temperature difference between the two reaction zones occurs within the intermediate bed. The length of the intermediate bed may also need to be chosen according to the amount of relatively high molecular weight by-products formed in the first reaction zone and the desired degree of removal of these by-products. These parameters can be determined, for example, by means of simple laboratory or pilot plant tests.

The inert material of the inert intermediate bed preferably has an empty volume fraction of from 40 to 99.5%, with the empty volume fraction being defined as: empty volume fraction=[(total volume)−(geometric volume)]/(total volume). Here, the "total volume" is the total volume of the inert intermediate bed in the reaction tube. The "geometric volume" is the macroscopic volume of the inert solid material including any pores present within the inert material. At an empty volume fraction below 40%, the pressure drop generally increases significantly. At an empty volume fraction greater than 99.5%, the desired effect of heating or cooling and the precipitation of relatively high molecular weight by-products is generally unsatisfactory. The empty volume fraction of the inert material is preferably from 45 to 99%.

Catalysts which can be used in the process of the present invention are in principle all catalysts suitable for the oxydehydrogenation of n-butenes to 1,3-butadiene and all catalysts suitable for the oxidation of 1,3-butadiene to maleic anhydride.

Particularly useful catalysts for the oxydehydrogenation of n-butenes to 1,3-butadiene are generally based on an Mo—Bi—O-containing multimetal oxide system which generally further comprises iron. In general, the catalyst system further comprises additional components from groups 1 to 15 of the Periodic Table, for example potassium, magnesium, zirconium, chromium, nickel, cobalt, cadmium, tin, lead, germanium, lanthanum, manganese, tungsten, phosphorus, aluminum or silicon.

Suitable catalysts and their production are described, for example, in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x$+$SiO_2$) and DE-A 24 40 329 ($Mo_{12}BiCo_{4.5}Ni_{2.5}Cr_3P_{0.5}K_{0.1}O_x$), which are explicitly incorporated by reference.

The stoichiometry of the active composition of many of the multimetal oxide catalysts suitable for the oxydehydrogenation of n-butenes to 1,3-butadiene can be described by the formula (I)

$$Mo_{12}Bi_aFe_bCo_cNi_dCr_eX^1_fK_gO_x \qquad (I),$$

where the variables have the following meanings:
$X^1$=W, Sn, Mn, La, Ce, Ge, Ti, Zr, Hf, Nb, P, Si, Sb, Al, Cd and/or Mg;
a=0.5 to 5, preferably from 0.5 to 2;
b=0 to 5, preferably from 2 to 4;
c=0 to 10, preferably from 3 to 10;
d=0 to 10;
e=0 to 10, preferably from 0.1 to 4;
f=0 to 5, preferably from 0.1 to 2;
g=0 to 2, preferably from 0.01 to 1; and
x=a number determined by the valence and abundance of the elements other than oxygen in (I).

In the process of the present invention, the oxydehydrogenation is preferably carried out using an Mo—Bi—Fe—O-containing multimetal oxide system, with an Mo—Bi—Fe—Cr—O- or Mo—Bi—Fe—Zr—O-containing multimetal oxide system being particularly preferred. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3Co_{4.5}Ni_{2.5}P_{0.5}K_{0.1}O_x$+$SiO_2$), DE-A 25 30 959 ($Mo_{12}BiFe_3Co_{4.5}Ni_{2.5}Cr_{0.5}K_{0.1}O_x$, $Mo_{13.75}BiFe_3Co_{4.5}Ni_{2.5}Ge_{0.5}K_{0.8}O_x$,  $Mo_{12}BiFe_3Co_{4.5}Ni_{2.5}Mn_{0.5}K_{0.1}O_x$ and $Mo_{12}BiFe_3Co_{4.5}Ni_{2.5}La_{0.5}K_{0.1}O_x$), U.S. Pat. No. 3,911,039 ($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$). Production and characterization of the catalysts mentioned are comprehensively described in the cited documents, which are hereby explicitly incorporated by reference.

The catalysts used for the oxidation of 1,3-butadiene to maleic anhydride are generally based on a multimetal oxide system comprising molybdenum oxide and preferably on an essentially Mo—Sb—O-containing or Mo—V—O-containing multimetal oxide system.

In the case of the Mo—Sb—O-containing multimetal oxide system, the catalyst system generally further comprises additional components from groups 1 to 8 and 14 of the Periodic Table and from the lanthanide series, for example lithium, titanium, vanadium, niobium, tungsten, iron, tin and cerium.

In the case of the Mo—Sb—O-containing multimetal oxide system, the active composition of many of the multimetal oxide catalysts suitable for the oxidation of 1,3-butadiene to maleic anhydride has the formula (II)

$$SbMo_aSn_bX^2{}_cO_x \quad (II),$$

where the variables have the following meanings:
$X^2$=V, Fe, Ni, Li, Ce, Nb, Ta, W, Ti, Zr, B, P, Al and/or Mg;
a=1 to 10, preferably from 2 to 4;
b=0 to 5, preferably from 0.01 to 2;
c=0 to 3, preferably from 0.01 to 1.5; and
x=a number determined by the valence and abundance of the elements other than oxygen in (II).

Suitable catalysts and their production are described, for example, in JP-A 05 057 188 ($Sb_2Mo_{10}O_x$ corresponding to $SbMo_5O_x$), DE-A 22 41 918 ($Sb_4Mo_{6.12}O_x$ corresponding to $SbMo_{1.53}O_x$), DE-A 23 22 186 ($SbMo_3V_{0.1}Fe_{0.2}W_{0.06}O_x$), DE 27 02 606 ($SbMo_3V_{0.1}Li_{0.1}W_{0.06}O_x$ and $SbMo_3V_{0.1}Ce_{0.1}W_{0.06}O_x$) and DE-A 28 13 424 ($SbMo_{3.06}T_{0.6}Nb_{0.1}O_x$). The production and characterization of the catalysts mentioned are comprehensively described in the cited documents, which are hereby explicitly incorporated by reference.

In the case of the Mo—V—O-containing multimetal oxide, the active composition of many of the multimetal oxide catalysts suitable for the oxidation of 1,3-butadiene to maleic anhydride has the formula (III)

$$Mo_{12}V_aW_bX^3{}_cO_x \quad (III),$$

where the variables have the following meanings:
$X^3$=La, Mn, Fe, Cu, Al, Co, Ni, Bi, Ag, P, Zn, Cd, As, Cr, Sn, U, Ti, Nb, Ge, alkali metal and/or alkaline earth metal;
a=0.1 to 12, preferably from 1.5 to 10;
b=0 to 5, preferably from 0.1 to 4;
c=0 to 12, preferably from 0.1 to 10; and
x=a number determined by the valence and abundance of the elements other than oxygen in (III).

Suitable catalysts and their production are described, for example, in U.S. Pat. No. 3,893,951 ($Mo_{12}V_3W_{1.2}O_x$, $Mo_{12}V_3W_{1.2}Sn_6O_x$), U.S. Pat. No. 4,157,987 ($Mo_{12}V_3W_{1.2}Ce_3O_x$, $Mo_{12}V_3W_{1.2}Ce_2CoO_x$, $Mo_{12}V_3W_{1.2}Ce_2Cu_2O_x$), DE-A 24 59 092 ($Mo_{12}V_3W_{1.2}U_2O_x$), U.S. Pat. No. 4,170,570 ($Mo_{12}V_3W_{1.2}Cu_2Sn_{0.5}O_x$), U.S. Pat. No. 4,378,309 ($Mo_{12}V_3Cu_{0.5}GeO_x$), U.S. Pat. No. 4,042,533 ($Mo_{12}V_3W_{1.2}Ti_{0.5}O_x$), U.S. Pat. No. 4,115,441 ($Mo_{12}V_3GeFe_{0.1}O_x$), U.S. Pat. No. 4,138,366 ($Mo_{12}V_3SbCd_{0.2}P_{0.1}O_x$), and U.S. Pat. No. 4,250,054 ($Mo_{12}V_3W_{1.2}La_{0.5}Co_{0.1}O_x$). Production and characterization of the catalysts mentioned are comprehensively described in the cited documents, which are hereby explicitly incorporated by reference.

The two catalysts for oxydehydrogenation and for oxidation are generally used as shaped bodies having a mean size of above 2 mm. Owing to the pressure drop, of which note has to be taken, when carrying out the process, relatively small shaped bodies are generally unsuitable. Suitable shaped bodies which may be mentioned are, for example, pellets, cylinders, hollow cylinders, rings, spheres, rods, wagon wheels or extrudates. Particular shapes such as "trilobes" and "tristars" (cf. EP-A-0 593 646) or shaped bodies having at least one constriction on the outside (cf. U.S. Pat. No. 5,168,090) are likewise possible.

In general, the catalysts to be used can be employed as all-active catalysts. In this case, the entire catalyst body consists of the active composition, including any auxiliaries such as graphite or pore formers, together with further components. In particular, the Mo—Bi—Fe—O-containing catalyst which is preferably used for the oxydehydrogenation of n-butenes to 1,3-butadiene is advantageously used as an all-active catalyst. It is also possible to apply the active compositions of the catalysts to a support, for example an inorganic, oxidic shaped body. Such catalysts are generally referred to as coated catalysts. In particular, the Mo—Sb—O- or Mo—V—O-containing catalyst which is preferably used for the oxidation of the 1,3-butadiene generated in the first step to maleic anhydride is advantageously used as a coated catalyst.

In the process of the present invention, the catalysts used in the two reaction zones are different catalysts, one of which is optimized for the oxydehydrogenation of n-butenes to 1,3-butadiene and the other is optimized for the oxidation of 1,3-butadiene to maleic anhydride. Likewise, the optimized reaction temperatures are set in each of the two reaction zones.

As regards the way the catalysts are installed in the first, feed-side reaction zone and in the second, product-side reaction zone in the process of the present invention, a number of variants are possible. In one variant, each reaction zone contains a homogeneous catalyst bed, i.e. a catalyst bed which has the same average composition and the same average activity per unit volume throughout the respective reaction zone. A catalyst bed can be made up of shaped bodies of the same catalyst, of shaped bodies of a mixture of various catalysts or of shaped bodies (same catalyst or mixture of various catalysts) which are mixed, i.e. "diluted", with an inert material. Suitable inert materials are in principle all shaped bodies which are also suitable for use in the preheating zones or as inert intermediate bed. Reference may be made to the information provided above.

In another variant, the first, feed-side reaction zone and/or the second, product-side reaction zone contain/contains a heterogeneous catalyst bed, i.e. a catalyst bed which has a composition and an activity per unit volume which vary over the length of the respective reaction zone. A heterogeneous catalyst bed is generally achieved by means of a heterogeneous mixture of various catalysts or shaped bodies (same catalyst or mixture of various catalysts) which are heterogeneously mixed, i.e. "diluted", with an inert material. The local activity within the reaction zone is thus set via the composition of the mixture. When using a heterogeneous catalyst bed, an increase in the activity in the flow direction of the reaction gas, i.e. from the feed side to the product side, is generally advantageous. The activity can increase uniformly in the flow direction of the reaction gas or can increase stepwise at one or more points.

In general, the optimized reaction temperature for the oxydehydrogenation of n-butenes to 1,3-butadiene is below that for the oxidation of 1,3-butadiene to maleic anhydride. This applies particularly when the catalyst used for the oxidation of 1,3-butadiene to maleic anhydride has the basic composition Mo—Sb—O. In the case of a corresponding Mo—V—O-based catalyst, specific compositions of this catalyst can result in the optimized reaction temperature for the oxydehydrogenation of n-butenes to 1,3-butadiene being above that for the oxidation of 1,3-butadiene to maleic anhydride.

In the present context, the reaction temperature is the temperature of the catalyst bed present in this reaction zone which would prevail if the process were carried out in the absence of a chemical reaction. If this temperature is not exactly the same at all points, the term refers to the arithmetic mean of the temperatures along the reaction zone. It thus corresponds approximately to the temperature of the surrounding heat transfer medium.

In the case of a catalyst having the basic composition Mo—Sb—O which is suitable for the oxidation of 1,3-butadiene to maleic anhydride in the second, product-side reaction zone, this is preferably operated at a reaction temperature which is at least 10° C. higher, particularly preferably at least 30° C. higher, than that of the catalyst which is suitable for the oxydehydrogenation of n-butenes to 1,3-butadiene in the first, feed-side reaction zone.

It is a specific feature of the process of the present invention that, depending on requirements, for example due to changes in the throughput over the catalyst or due to ageing of the catalysts, the reaction temperatures of the two reaction zones can be regulated independently.

The oxydehydrogenation of n-butenes to 1,3-butadiene in the first, feed-side reaction zone in the process of the present invention is generally carried out at from 220 to 490° C., preferably from 250 to 450° C.

The oxidation of 1,3-butadiene to maleic anhydride in the second, product-side reaction zone in the process of the present invention is generally carried out at from 190 to 500° C., preferably from 230 to 460° C.

As regards the reaction pressure, there are generally no particular requirements in the process of the present invention. For practical reasons, it is normal to select a pressure at the inlet of the reactor which is sufficient to overcome the flow resistances present in the plant and in the subsequent work-up. This reactor inlet pressure is generally from 0.005 to 1 MPa gauge pressure, preferably from 0.01 to 0.5 MPa gauge pressure. The gas pressure employed at the inlet region of the reactor naturally drops significantly over the bed of catalysts and inert sections.

n-Butene-containing hydrocarbon streams used in the process of the present invention are generally hydrocarbon streams which have a total n-butene content (1-butene, 2-trans-butene and 2-cis-butene) of ≧10% by weight, preferably ≧30% by weight. The n-butene-containing hydrocarbon stream may further comprise aliphatic and aromatic, saturated and unsaturated hydrocarbons. Examples which may be mentioned are methane, ethane, ethene, propane, propene, 1,3-butadiene, n-butane, isobutane, isobutene, 1,3-pentadiene, 1,4-pentadiene, 1-pentene, 2-cis-pentene, 2-trans-pentene, n-pentane, cyclopentadiene, dicyclopentadiene, cyclopentene, cyclopentane, hexenes, hexanes, cyclohexane and benzene.

The n-butene-containing hydrocarbon streams used in the process of the present invention are preferably streams from natural gas, steam crackers or FCC plants. Particular preference is given to raffinate II which is obtained from the crude $C_4$ fraction from steam crackers. Raffinate II is the $C_4$ stream from which 1,3-butadiene has been largely removed or converted into n-butenes by selective hydrogenation and isobutene has been removed. Its n-butene content is generally from 50 to 95% by weight. A typical but nonlimiting composition of a raffinate II stream is given in Table 1:

TABLE 1

Typical composition of a raffinate II stream.

| | Raffinate II |
|---|---|
| 1-butene | from 20 to 60% by weight |
| 2-trans-butene | from 10 to 30% by weight |
| 2-cis-butene | from 5 to 20% by weight |
| n-butane | from 5 to 35% by weight |
| isobutane | from 1 to 10% by weight |
| isobutene | from 1 to 2% by weight |

The addition of the hydrocarbons is generally quantity-regulated, i.e. regulated so that a defined amount is added per unit time. The hydrocarbon can be metered in in liquid or gaseous form. Preference is given to metering in the hydrocarbon in liquid form and subsequently vaporizing it before entry into the shell-and-tube reactor.

The oxygen-containing gas used in the process of the present invention is generally air, synthetic air, an oxygen-enriched gas or "pure" oxygen, for example oxygen from the fractionation of air. The oxygen-containing gas, too, is added in a quantity-regulated manner.

The gas to be passed through the two reaction zones generally comprises inert gas. The proportion of inert gas at the beginning is usually from 30 to 95% by volume. Inert gases are all gases which do not contribute directly to the formation of maleic anhydride, for example nitrogen, steam, noble gases, carbon monoxide, carbon dioxide, oxygenated and nonoxygenated hydrocarbons containing less than four carbon atoms, e.g. methane, ethane, propane, methanol, formaldehyde, formic acid, ethanol, acetaldehyde, acetic acid, propanol, propionaldehyde, propionic acid, acrolein, crotonaldehyde, acrylic acid) and mixtures thereof. In general, the inert gas is introduced into the system via the oxygen-containing gas. However, it is also possible for further inert gases to be fed in separately. Thus, for example, the process of the present invention can be carried out with introduction of generally up to 50% by weight of steam. The process of the present invention is preferably carried out without introduction of additional inert gases.

The process of the present invention is generally carried out in a "single pass". The reaction gas used generally comprises from 0.1 to 30% by volume, preferably from 0.5 to 7% by volume, of n-butenes and from 5 to 50% by volume, preferably from 10 to 40% by volume, of oxygen. The conversion of n-butenes is generally from 50 to 100%, preferably from 75 to 100% and particularly preferably from 85 to 100%. The unreacted n-butenes can be separated from the maleic anhydride formed and further products and then recirculated to the initial feed. Preference is given to operating the process in a single pass with a very high n-butene conversion and no recirculation of unreacted n-butenes.

The maleic anhydride can be separated off by, for example, absorption in a suitable absorption medium. Suitable absorption media are, for example, water or organic solvents. In the case of absorption in water, maleic anhydride is hydrated to form maleic acid. Preference is given to absorption in an organic solvent. Suitable organic solvents are, for example, the high-boiling solvents mentioned in WO 97/43242, for example tricresyl phosphate, dibutyl maleate, high molecular weight wax, aromatic hydrocarbons having a boiling point above 140° C. or di-$C_4$–$C_8$-alkyl phthalates such as dibutyl phthalate. Oxygenated hydrocarbon by-products are generally also absorbed in the solvents mentioned. The absorption can be carried out, for example, at from 60 to 160° C. and a pressure of from 0.1 to 0.5 MPa abs or above. Suitable methods are, for instance, passing the gaseous, cooled or uncooled reactor output through a vessel filled with absorption liquid or spraying the absorption liquid into the gas stream. Appropriate methods of scrubbing gas streams are known to those skilled in the art.

Furthermore, we have found the use of a shell-and-tube reactor having two successive reaction zones and at least one heat transfer medium circuit in the region of the first, feed-side reaction zone and at least one further heat transfer medium circuit in the region of the second, product-side reaction zone in the heterogeneously catalyzed gas-phase oxidation of an n-butene-containing hydrocarbon stream by means of oxygen to form maleic anhydride.

Preference is given to the use of a shell-and-tube reactor having two successive reaction zones and one heat transfer medium circuit in the region of the first, feed-side reaction zone and a further heat transfer medium circuit in the region of the second, product-side reaction zone in the heterogeneously catalyzed gas-phase oxidation of an n-butene-containing hydrocarbon stream by means of oxygen to form maleic anhydride.

A description is given below of a preferred embodiment of the preparation of maleic anhydride by heterogeneously catalyzed gas-phase oxidation of an n-butene-containing hydrocarbon stream by means of an oxygen-containing gas in a shell-and-tube reactor having two successive reaction zones and having a heat transfer medium circuit in the region of the first feed-side-reaction zone and a further heat transfer medium circuit in the region of the second, product-side reaction zone.

The heat transfer medium flows from the bottom upward through each of the two heat transfer medium circuits of the shell-and-tube reactor. The shell-and-tube reactor is operated in cocurrent, i.e. the reaction gas (feed gas) is fed in from the bottom. The reaction gas used is a gas mixture of raffinate II in air having an n-butene content of from 0.5 to 7% by volume. In the lowermost zone of the bed, which functions as preheating zone, the shell-and-tube reactor contains inert material. The next zone of the bed in an upward direction, viz. the first reaction zone, contains the catalyst for the oxydehydrogenation of the n-butenes to 1,3-butadiene, which comprises an Mo—Bi—Fe—O-containing multimetal oxide system as active composition. The first reaction zone is operated in a temperature range from 250 to 450° C. In the region of or in the vicinity of the dividing plate located in the shell-and-tube reactor to separate the two heat transfer medium circuits, there is an inert intermediate bed having an empty volume fraction in the range from 40 to 99.5%. The following, second reaction zone contains the catalyst for the oxidation of 1,3-butadiene to maleic anhydride, which comprises an Mo—Sb—O-containing or Mo—V—O-containing multimetal oxide system as active composition. The second reaction zone is operated in a temperature range from 230 to 460° C. The pressure of the reaction gas at the reactor inlet is in the range from 0.01 to 0.5 MPa gauge pressure. Temperature and space velocity over the catalyst are generally selected so that an overall conversion of n-butenes of $\geq 50\%$, preferably $\geq 75\%$ and particularly preferably $\geq 85\%$, results. The reaction gas taken off at the top of the reactor is passed to an absorption stage to separate off the maleic anhydride formed.

The process of the present invention makes it possible to achieve a high conversion, a high selectivity, a high yield of desired product and thus a high space-time yield in the preparation of maleic anhydride by heterogeneously catalyzed gas-phase oxidation using an inexpensive and readily available hydrocarbon stream at a high hydrocarbon throughput over the catalyst. Due to the two heat transfer medium circuits which allow the temperature in the two reaction zones to be regulated separately, the process of the present invention can be carried out flexibly so as to make it possible to achieve a high space-time yield over a long period of time even in the case of fluctuations in the amount, quality or purity of starting materials or in the event of progressive catalyst deactivation. Compared to a process carried out in two shell-and-tube reactors connected in series, carrying out the process in a single shell-and-tube reactor having two successive reaction zones leads to considerable capital cost savings and to a significant simplification of the overall plant.

In addition, the inert intermediate bed located between the first, feed-side reaction zone and the second, product-side reaction zone in a preferred variant of the process of the present invention makes it possible for relatively high molecular weight by-products from the first reaction zone, for example oligomers, polymers or carbon, to be precipitated and counters deposition on the catalyst of the second reaction zone and thus a gradual increase in the pressure drop caused by such deposits on the catalyst.

The maleic anhydride obtained can, for example, be processed further to produce γ-butyrolactone, tetrahydrofuran, 1,4-butanediol or mixtures thereof. Suitable processes are known to those skilled in the art. For the sake of completeness, reference is made to the two documents WO 97/43234 (direct hydrogenation of maleic anhydride in the gas phase) and WO 97/43242 (hydrogenation of a maleic diester in the gas phase).

EXAMPLES

Definitions

The parameters referred to in this text are, unless indicated otherwise, defined as follows:

$$\text{Conversion } C = \frac{n_{HC,reactor,in} - n_{HC,reactor,out}}{n_{HC,reactor,in}}$$

$$\text{Selectivity } S_{MA} = \frac{n_{MA,reactor,out}}{n_{HC,reactor,in} - n_{HC,reactor,out}}$$

Yield $Y_{MA} = U \cdot S_{MA}$

C Conversion of hydrocarbons per pass through the reactor $S_{MA}$ Selectivity to maleic anhydride per pass through the reactor $Y_{MA}$ Yield of maleic anhydride per pass through the reactor $n_{HC, reactor, in}$ Molar flow of hydrocarbons at the reactor inlet [mol/h]

$n_{HC, reactor, out}$ Molar flow of hydrocarbons at the reactor outlet [mol/h]

$n_{HC, plant, in}$ Molar flow of hydrocarbons at the inlet to the plant [mol/h]

$n_{HC, plant, out}$ Molar flow of hydrocarbons at the outlet of the plant [mol/h]

$n_{HC, reactor, out}$ Molar flow of maleic anhydride at the reactor outlet [mol/h]

$n_{MA, plant, out}$ Molar flow of maleic anhydride at the outlet of the plant [mol/h]

Production of the Oxydehydrogenation Catalyst K1

1750.9 g of aqueous cobalt nitrate solution having a free $HNO_3$ content of 0.2% by weight and a Co content of 12.5% by weight (=3.71 mol of Co) were placed in a heatable 10 l stirred vessel made of glass. While stirring, 626.25 g of solid Fe(NO$_3$)$_3$.9H$_2$O having an Fe content of 14.2% by weight (=1.59 mol of Fe) were dissolved at room temperature in the initial charge of cobalt nitrate solution. 599.5 g of bismuth nitrate solution having a free HNO$_3$ content of 3% by weight and a Bi content of 11.1% by weight (=0.32 mol of Bi) were added at room temperature to the resulting solution. 106.23 g of solid Cr(NO$_3$)$_3$.9H$_2$O (=0.27 mol of Cr) were subsequently added. After heating to 60° C. and further stirring, a red solution (solution A) was obtained.

A further heatable 3 l stirred vessel made of glass was charged with 2000 ml of water. 2.38 g of KOH (=0.042 mol of K) and 1124.86 g of (NH$_4$)$_6$Mo$_7$O$_{24}$.4H$_2$O (=6.37 mol of Mo) were subsequently added and dissolved at 60° C. The solution obtained was slightly turbid (solution B).

Solution B was subsequently pumped into solution A, with the latter being stirred. 102.05 g of SiO$_2$ sol having an SiO$_2$ content of 50% by weight ("Ludox TM", from DuPont) (=0.85 mol of Si) were added to the resulting dark yellow suspension at 60° C.

The suspension obtained was stirred at 60° C. for another 30 minutes and subsequently spray dried (inlet temperature: 370° C., outlet temperature: 110–112° C.). The spray-dried powder obtained was admixed with 4% by weight of graphite and subsequently tabletted to form solid pellets having a diameter of 5 mm and a height of 3 mm. The solid pellets were heated at 480° C. for 6 hours on a wire screen (mesh opening: 3.5 mm) through which 100 l/h of air was passed in a muffle furnace. The calcined pellets were broken up on a wire screen to give catalyst granules K1 having an average granule diameter of 2–3 mm.

The oxydehydrogenation catalyst K1 had the nominal composition Mo$_{12}$Bi$_{0.6}$Fe$_3$Co$_7$Cr$_{0.5}$Si$_{1.6}$K$_{0.08}$O$_x$.

Production of the Oxidation Catalyst K2

2500 ml of water were placed in a heatable 10 l stirred vessel made of glass and 226.72 g of MoO$_3$ (from Fluka) (=1.575 mol of Mo), 25.17 g of TiO$_2$ ("Finn Ti S 150", from Kemira) (=0.315 mol of Ti), 6.99 g of Nb$_2$O$_5$ (from H.C. Starck) (=0.052 mol of Nb) and 21.7 g of SnC$_2$O$_4$ (from Merck) (=0.105 mol of Sn) were added. The suspension obtained was refluxed for 2 hours. After addition of 76.52 g of Sb$_2$O$_3$ (from Merck) (=0.52 mol of Sb), the suspension was refluxed for another 16 hours and subsequently cooled to 50° C. 35 g of an aqueous Acronal solution having an Acronal content of 50% by weight (water-soluble polymer based on acrylic acid, from BASF) were then added, followed by addition of 140 g of formamide (from BASF).

To produce a coated catalyst, the resulting suspension was sprayed by means of a two-fluid nozzle onto 750 g of steatite spheres having a mean diameter of 2.5–3.2 mm (from Ceramtec). During the coating procedure, the steatite spheres were kept in motion in a coating drum which had an internal diameter of 300 mm and was maintained at 150° C. and rotated at 60 revolutions per minute. This resulted in a coated catalyst K2 having an active composition content of 31% by weight.

The oxidation catalyst had the nominal composition SbMo$_{3.06}$Ti$_{0.6}$Nb$_{0.1}$Sn$_{0.2}$O$_x$.

Experimental Plant E1

The experimental plant was equipped with a feed unit and a reactor tube having two electrically operated heating zones which could be regulated separately. A tube reactor having electrically operated heating zones can readily be used on a laboratory or pilot plant scale to replace a shell-and-tube reactor whose temperature is regulated by means of heat transfer medium circuits.

The reactor tube used had a length of 2 m and an internal diameter of 12 mm. The feed was passed through the upright reactor tube from the bottom upward. The lower end of the reactor tube was provided with a mesh to support the beds. The reactor tube contained the following five bed zones, from the bottom upward:

| | |
|---|---|
| Bed zone A (bottom): | 15 cm of steatite spheres having a mean diameter of 2–3 mm. |
| Bed zone B: | 80 cm of oxydehydrogenation catalyst K1. |
| Bed zone C: | 30 cm od steatite spheres having a mean diameter of 2–3 mm. |
| Bed zone D: | 65 cm of oxidation catalyst K2. |
| Bed zone E (top): | 10 cm steatite spheres having a mean diameter of 2–3 mm. |

The bed zones A and B were located in the first heating zone and were maintained at a temperature T$_1$, with the bed zone A functioning as preheating zone for the oxydehydrogenation zone. The bed zones C, D and E were located essentially in the second heating zone and were maintained at the temperature T$_2$, with the bed zone C ("inert intermediate bed") functioning as preheating zone for the oxidation zone and making it possible to precipitate relatively high molecular weight by-products from the first reaction zone.

The experimental plant was operated in a single pass. The reaction gas leaving the upper end of the reactor was analyzed by gas chromatography.

As feed gas stream, a mixture of 2% by volume of n-butenes (mixture of 60% of 1-butene and 40% of 2-butenes) in air was fed in. The feed gas was introduced at a rate of 140 standard l/h, which corresponds to a GHSV of 1600 standard l/[(l of catalyst K1).h]. The pressure at the upper reactor outlet was 0.01 MPa gauge pressure.

Example 1 (According to the Present Invention)

In example 1, the optimum reaction temperatures were set for both reactions. The oxydehydrogenation over K1 was carried out at T$_1$=330° C. and the oxidation over K2 was carried out at T$_2$=400° C.

The values shown in table 2 were determined after a running-in time of 3 days.

Example 2 (Comparative Example)

In example 2, the optimum temperature for the oxydehydrogenation over K1 was set in both the reaction zones. T$_1$ and T$_2$ were thus 330° C. The values shown in table 2 were determined after a running-in time of 3 days.

Example 3 (Comparative Example)

In example 3, the optimum temperature for the oxidation over K2 was set in both the reaction zones. T$_1$ and T$_2$ were thus 400° C. The values shown in table 2 were determined after a running-in time of 3 days.

TABLE 2

Results from examples 1 to 3

| Example | $T_1$ [° C.] | $T_2$ [° C.] | C [%] | $Y_{MA}$ [%] |
|---|---|---|---|---|
| 1 | 330 | 400 | 99 | 62 |
| 2* | 330 | 330 | 99 | 32 |
| 3* | 400 | 400 | 99 | 54 |

*comparative example

Example 1 according to the present invention shows that optimum temperatures in the two successive reaction zones, as can be realized in a shell-and-tube reactor having one heat transfer medium circuit in the region of the first, feed-side reaction zone and a further heat transfer medium circuit in the region of the second, product-side reaction zone, results in a significantly higher yield of maleic anhydride than in the two comparative examples in which the temperature is the same in both the reaction zones.

We claim:

1. A process for preparing maleic anhydride by heterogeneously catalyzed gas-phase oxidation of an n-butene-containing hydrocarbon stream by means of oxygen-containing gases in a shell-and-tube reactor, which comprises conducting the gas-phase oxidation of the n-butene-containing hydrocarbon stream in a shell-and-tube reactor which has two successive reaction zones (a) and (b), (a) being the first, feed-side reaction zone and containing at least one catalyst which is suitable for oxydehydrogenating n-butenes to obtain 1,3-butadiene, and (b) being the second, product-side reaction zone and containing at least one catalyst which is suitable for oxidizing 1,3-butadiene to obtain maleic anhydride, and wherein the shell-and-tube reactor has, in the region of each of the reactions zones (a) and (b), at least one heat transfer medium circuit which is separate and independent from the heat transfer medium circuit of the other reaction zone.

2. A process as claimed in claim 1, wherein the reaction gas from the first, feedside reaction zone is passed through an inert intermediate bed before it enters the second, product-side reaction zone.

3. A process as claimed in claim 2, wherein the inert intermediate bed used is a bed of inert material having an empty volume fraction of from 40 to 99.5%.

4. A process as claimed in claim 1, wherein the active composition of the catalyst suitable for the oxydehydrogenation of n-butenes to 1,3-butadiene is a multimetal oxide of the formula (I)

$$Mo_{12}Bi_aFe_bCo_cNi_dCr_eX^1_fK_gO_x \qquad (I),$$

where the variables have the following meanings:

$X^1$=W, Sn, Mn, La, Ce, Ge, Ti, Zr, Hf, Nb, P, Si, Sb, Al, Cd and/or Mg;
a=0.5 to 5;
b=0 to 5;
c=0 to 10;
d=0 to 10;
e=0 to 10;
f=0 to 5;
g=0 to 2; and
x=a number determined by the valence and abundance of the elements other than oxygen in (I).

5. A process as claimed in claim 1, wherein the active composition of the catalyst suitable for the oxidation of 1,3-butadiene to maleic anhydride is a multimetal oxide of the formula (II)

$$SbMo_aSn_bX^2_cO_x \qquad (II),$$

where the variables have the following meanings:

$X^2$=V, Fe, Ni, Li, Ce, Nb, Ta, W, Ti, Zr, B, P, Al and/or Mg;
a=1 to 10;
b=0 to 5;
c=0 to 3; and
x=a number determined by the valence and abundance of the elements other than oxygen in (II).

6. A process as claimed in claim 1, wherein the active composition of the catalyst suitable for the oxidation of 1,3-butadiene to maleic anhydride is a multimetal oxide of the formula (III)

$$Mo_{12}V_aW_bX^3_cO_x \qquad (III),$$

where the variables have the following meanings:

$X^3$=La, Mn, Fe, Cu, Al, Co, Ni, Bi, Ag, P, Zn, Cd, As, Cr, Sn, U, Ti, Nb, Ge, an alkali metal and/or an alkaline earth metal;
a=0.1 to 12;
b=0 to 5;
c=0 to 12; and
x=a number determined by the valence and abundance of the elements other than oxygen in (III).

7. A process as claimed in claim 1, wherein the oxydehydrogenation of n-butenes to 1,3-butadiene in the first, feed-side reaction zone is carried out at from 220 to 490°C. and the oxidation of 1,3-butadiene to maleic anhydride in the second, product-side reaction zone is carried out at from 190 to 500°C.

8. A process as claimed in claim 1, wherein the pressure at the reactor inlet is from 0.005 to 1 MPa gauge pressure.

9. A process as claimed in claim 1, wherein the n-butene-containing hydrocarbon stream used is a raffinate II stream.

* * * * *